United States Patent
Gately

(10) Patent No.: US 6,861,531 B2
(45) Date of Patent: Mar. 1, 2005

(54) SYNTHESIS OF 2,6-DICARBONYLPYRIDINES

(75) Inventor: Daniel A. Gately, Berthoud, CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 10/405,464

(22) Filed: Apr. 2, 2003

(65) Prior Publication Data

US 2004/0063958 A1 Apr. 1, 2004

Related U.S. Application Data

(62) Division of application No. 10/107,648, filed on Mar. 27, 2002.

(51) Int. Cl.$^7$ .............................................. C07D 211/70
(52) U.S. Cl. ........................................................ 546/314
(58) Field of Search .......................................... 546/314

(56) References Cited

U.S. PATENT DOCUMENTS 4,523,018 A * 6/1985 Kumagae et al. ........... 546/315

* cited by examiner

*Primary Examiner*—Patricia L. Morris
(74) *Attorney, Agent, or Firm*—Aileen Law; Patent Law Offices of Rick Martin, P.C.

(57) ABSTRACT

Synthesis of 2,6-dicarbonylpyridines in solution in a hydrocarbon medium is described. The solutions of 2,6-dicarbonylpyridines may be used directly in further syntheses.

1 Claim, No Drawings

SYNTHESIS OF 2,6-DICARBONYLPYRIDINES

This application is a division of U.S. application Ser. No. 10/107,648 now abandoned, filed Mar. 27, 2002.

FIELD OF THE INVENTION

This invention relates to the synthesis of 2,6-dicarbonylpyridine dihalides and to conversion of such dihalides to 2,6-dicarbonylpyridines. More specifically, this invention relates to the synthesis of 2,6-diacetylpyridine.

BACKGROUND OF THE INVENTION 2,6-diacetylpyridine has been prepared from reaction of pyridine 2,6-dicarboxylic acid diethyl ester and ethyl acetate in the presence of sodium ethoxide, ethanol and xylene. See Lukes, et al., *Collect. Czech Chem. Commun.* 24:36 (1959). A 55% to 57% yield for this reaction is reported by Terentew, et al., *Zh. Vses. Khim. Ova im. D. I. Mendeleeva* 6:116 (1961) (Abstract), CAOLD Abstract CA 55:144501. An analogous, presently commercial, multi-step synthesis is generally illustrated by Equation 1:

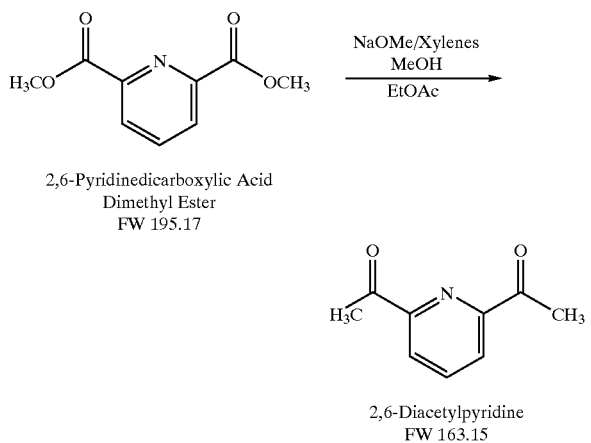

EQUATION 1

2,6-Pyridinedicarboxylic Acid Dimethyl Ester
FW 195.17

2,6-Diacetylpyridine
FW 163.15

2,6-diacetylpyridine in about 50% yield may be extracted by solvent exchange from the reaction mixture.

Yamamoto, *Chem. Pharm. Bull.* 43:1028–1030 (1995) reports a 59% yield of 2,6-diacetylpyridine by reaction of 2,6-bis(trimethyl stannyl) pyridine with 2-oxo-propenyl chloride. Reaction of 2,6-pyridine carbonyl chloride with methyl lithium in the presence of CuI at −78° C. in THF is said to provide a 93% yield of 2,6-diacetylpyridine. Jiang, et al., *Tetrahedron Lett.* 37(6):797–800 (1996). Organocupritic intermediates decompose rapidly if a uniform low temperature, impractical in a large reactor, is not maintained.

There is a need for a cost effective synthesis free of low temperature parameters that provides a high yield of 2,6-diacetylpyridine in a reaction mixture which may but need not be used directly in further syntheses.

SUMMARY OF THE INVENTION

Pursuant to one specific aspect of the invention, a 2,6-pyridine dicarboxylic acid is converted to a corresponding 2,6-dicarbonyl dichloride in hydrocarbon solution. The dichloride is converted in situ to a 2,6-pyridine-bis(2-alkoxyalkyl) carboxamide. The carboxamide may be treated sequentially first with a hydrocarbyl alkali metal salt, and thereafter with a trialkyl silicon halide. Treatment of the consequent reaction mixture with water yields a biphasic solution comprising an aqueous bottom layer and an organic top layer containing the desired 2,6-dicarbonylpyridine. An additional quantity of 2,6-dicarbonylpyridine may be recovered from the aqueous layer by extraction with toluene.

GENERAL DESCRIPTION OF THE INVENTION

Pursuant to a typical first step of the invention, a 2,6-pyridine dicarboxylic acid is converted in known manner to any corresponding 2,6-pyridine dicarboxylic dihalide, preferably a dichloride. For example, the 2,6-pyridine dicarboxylic acid may be treated with a sulfonyl halide, such as sulfonyl chloride, in a hydrocarbon medium, preferably toluene, for a time and under conditions effective to yield a solution of the corresponding 2,6-pyridine dicarboxylic acid dihalide in the hydrocarbon medium.

The hydrocarbon medium solution of 2,6-pyridine dicarboxylic acid dihalide may be taken up in a $C_1$ to $C_5$ alkyl halide, preferably methylene chloride, medium and treated with a bis(2-alkoxyalkyl) amine, preferably bis(2-methoxyethyl) amine, and a $C_1$ to $C_5$ trialkyl amine to produce a reaction mixture comprising 2,6-pyridine dicarboxamide in a mixed hydrocarbon and alkyl halide medium. The bis(2-alkoxyalkyl) amine and the trialkyl amine are preferably premixed but may be added separately in any desired sequence. The alkyl halide component of this mixed medium may be stripped from the reaction mixture to provide a solution of the 2,6-pyridine dicarboxamide in the residual hydrocarbon.

A second step of the invention may comprise treatment of the hydrocarbon solution of 2,6-pyridine dicarboxamide from the first step with an alkyl or aryl alkali metal salt having the formula RM, in which R comprises any alkyl or aryl group and M comprises any alkali metal. Preferably, R comprises a $C_1$ to $C_6$ alkyl group or a $C_6$ to $C_{10}$ substituted or unsubstituted aryl group. Methyllithium is preferred. A typical second step reaction is illustrated by Equation 2:

EQUATION 2

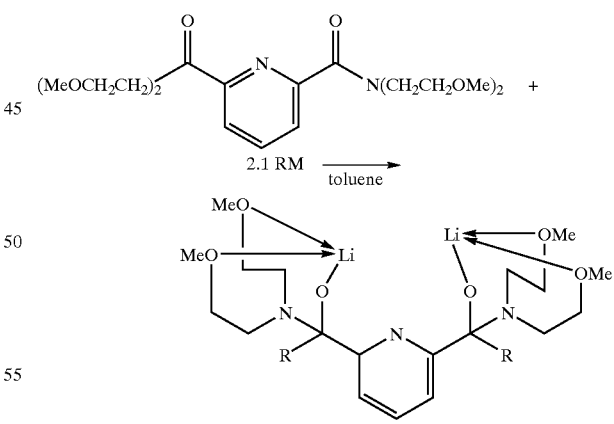

The reaction of the carboxamide with the alkali metal salt proceeds in two stages.

In a first stage, the exotherm may be controlled to provide a pot temperature range of −25° C. to −15° C. The pot temperature of the first stage reaction mixture is preferably adjusted to and maintained at a temperature of −10° C. to −30° C. for a short time, for example, for 15 to 45 minutes, and thereafter cooled to a pot temperature in the range of −10° C. to −20° C. The cooled first stage reaction mixture may be treated with any desired trialkylsilyl halide, typically trimethylsilyl chloride (TMSCl), in a hydrocarbon medium as the consequent exotherm is controlled to provide and maintain a pot temperature in the range of –10° C. to 10° C.

The second stage reaction is generally illustrated by Equation 3:

EQUATION 3

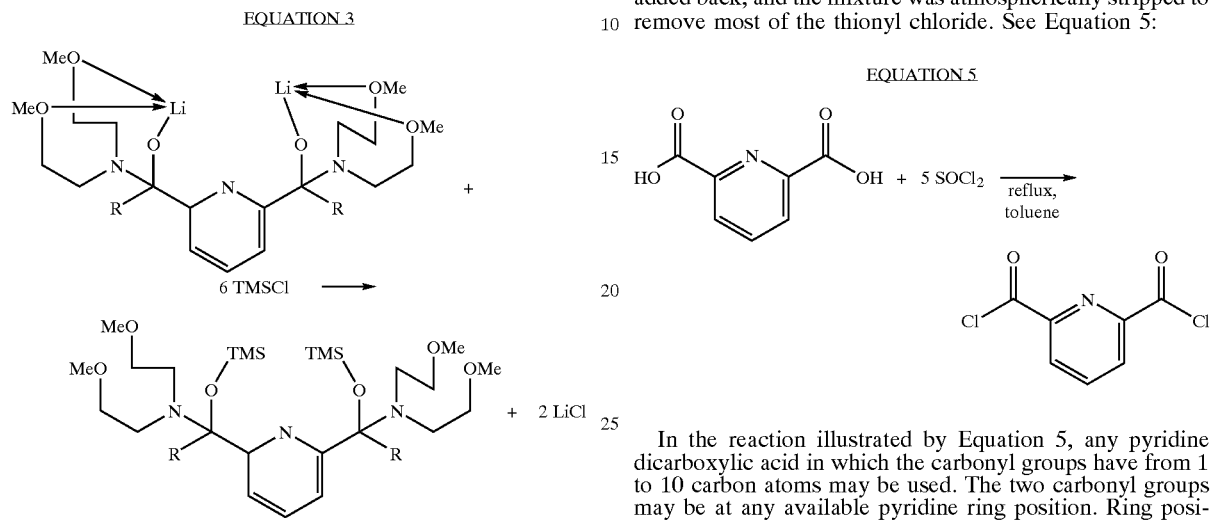

The second stage reaction mixture is a slurry in the first stage hydrocarbon medium. It may be transferred to a separate vessel containing iced water as the exotherm is controlled to provide and maintain a pot temperature of 0° C. to 15° C. The reaction is illustrated by Equation 4:

EQUATION 4

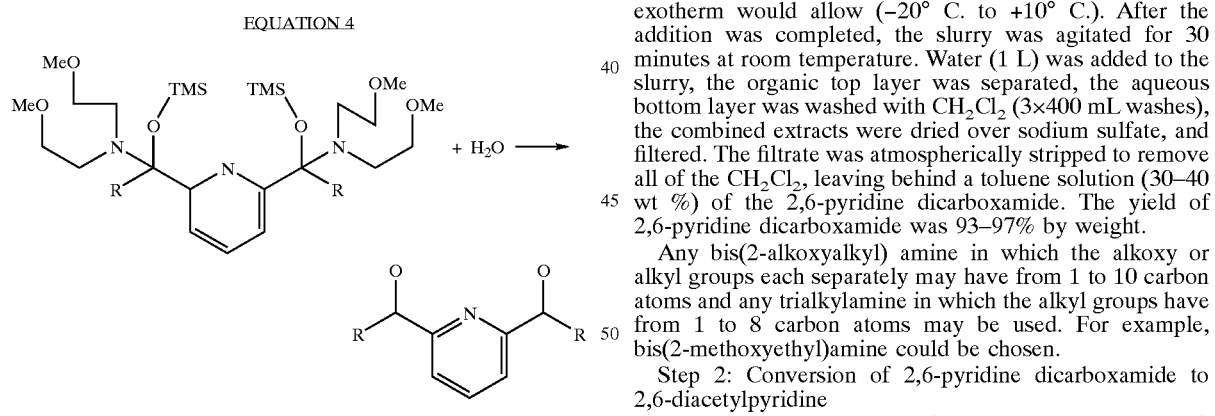

The pot temperature of the consequent biphasic solution comprising an aqueous bottom layer and an organic top layer may be adjusted to room temperature. The organic top layer comprises a hydrocarbon solution of the desired 2,6-dicarbonylpyridine. The aqueous bottom layer may be separated and washed with toluene to provide an extract containing an additional quantity of 2,6-dicarbonylpyridine which may be added to the separated organic top layer. Yields from the last step range from 85% to 90% by weight based on the 2,6-dicarboxylic acid starting material. Overall yields of 2,6-dicarbonylpyridine from all three steps typically are 80–83% by weight.

EXEMPLIFICATION OF THE INVENTION

Example 1

Step 1: Synthesis of 2,6-Pyridine Dicarboxamide

A 5 L flask, charged with 2,6-pyridine dicarboxylic acid (167 g, 1 mol), toluene (400 mL), and thionyl chloride (594 g, 5 mol), was refluxed. The excess thionyl chloride was atmospherically stripped so that the pot temperature was held at 120° C. to 130° C. for 30 minutes. Toluene (1 L) was added back, and the mixture was atmospherically stripped to remove most of the thionyl chloride. See Equation 5:

EQUATION 5

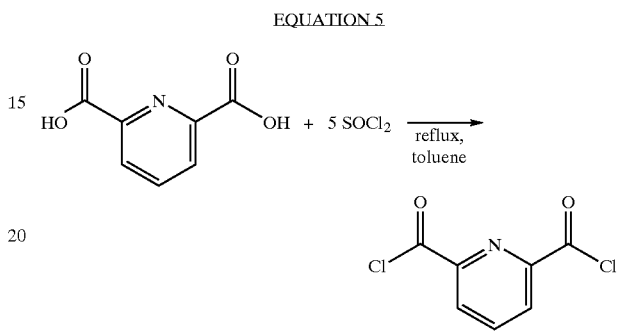

In the reaction illustrated by Equation 5, any pyridine dicarboxylic acid in which the carbonyl groups have from 1 to 10 carbon atoms may be used. The two carbonyl groups may be at any available pyridine ring position. Ring positions not occupied by carbonyl groups may have any other desired substituents. $C_1$ to $C_{10}$ alkyl substituents are preferred.

The intermediate 2,6-pyridine diacetyl chloride (in about 200–300 mL of toluene) was cooled to room temperature and taken up into $CH_2Cl_2$ (1 L). The yield of 2,6-diacetyl chloride was quantitative.

The $CH_2Cl_2$ solution was cooled (–20° C.), and treated with a premixed solution of bis(2-methoxyethyl) amine (270 g, 2.03 mol) and triethylamine (253 g, 2.5 mol) as fast as the exotherm would allow (–20° C. to +10° C.). After the addition was completed, the slurry was agitated for 30 minutes at room temperature. Water (1 L) was added to the slurry, the organic top layer was separated, the aqueous bottom layer was washed with $CH_2Cl_2$ (3×400 mL washes), the combined extracts were dried over sodium sulfate, and filtered. The filtrate was atmospherically stripped to remove all of the $CH_2Cl_2$, leaving behind a toluene solution (30–40 wt %) of the 2,6-pyridine dicarboxamide. The yield of 2,6-pyridine dicarboxamide was 93–97% by weight.

Any bis(2-alkoxyalkyl) amine in which the alkoxy or alkyl groups each separately may have from 1 to 10 carbon atoms and any trialkylamine in which the alkyl groups have from 1 to 8 carbon atoms may be used. For example, bis(2-methoxyethyl)amine could be chosen.

Step 2: Conversion of 2,6-pyridine dicarboxamide to 2,6-diacetylpyridine

The step 1 reaction mixture (2,6-pyridine dicarboxamide) (372 g as a 35 wt % solution in toluene, 0.937 mol) was cooled (–25° C.) and MeLi (1.4 M, 1.97 mol, 2.1 equivalents, 1.4 L) was added as fast as the exotherm would allow (temperature range –25° C. to –15° C.). After the addition, the solution was warmed to –10° C. to –5° C. for 30 minutes, the solution was cooled (–10° C.), and treated with trimethylsilyl chloride (TMSCl (611 g, 5.62 mol)) (see Equation 3) as fast as the exotherm would allow (–10° C. to +10° C. The resulting slurry was warmed to room temperature for 30 minutes and cooled (–10° C.). The slurry was transferred to a flask containing iced water (1.5 L) as fast as the exotherm maintained at 0° C. to 15° C. would allow. The biphasic solution was warmed to room temperature, the organic top layer was separated, the aqueous bottom layer was washed (3×350 mL) with toluene, and the combined extracts were dried over sodium sulfate and filtered. The filtrate was atmospherically stripped to remove hexamethyldisiloxane which resulted from the reaction of trimethylsilyl chloride with water (Equation 6):

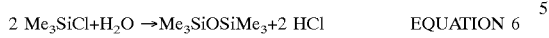

$$2\ Me_3SiCl + H_2O \rightarrow Me_3SiOSiMe_3 + 2\ HCl \qquad \text{EQUATION 6}$$

and polish-filtered at room temperature so that the desired product remained in toluene as a solution (25 to 30 wt %) useful directly in subsequent syntheses. Yields from the !last step range from 85 to 90%, and the overall yields from 2,6-dicarboxylic acid of all three steps are 80–83%.

Any alkyl or aryl alkali metal salt heretofore described may be used instead of methyllithium. Any desired trialkyl silicon halide may be used instead of trimethylsilyl chloride.

What is claimed is:

1. A process for synthesizing a compound of the formula

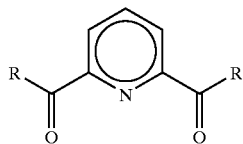

wherein R comprises an alkyl or aryl group, said process comprising:

treating a 2,6-pyridine dicarboxylic dihalide in solution in a hydrocarbon medium with a bis(2-alkoxyalkyl) amine and a trialkyl amine, whereby a reaction mixture containing a 2,6-pyridine dicarboxamide in said hydrocarbon medium is produced;

treating said 2,6-pyridine dicarboxamide in solution in said hydrocarbon medium with a compound of formula RM, wherein R comprises a $C_1$ to $C_6$ alkyl group or a $C_6$ to $C_{10}$ substituted or unsubstituted aryl group and M comprises an alkali metal, whereby a first reaction mixture is produced;

treating said first reaction mixture with a trialkylsilyl halide, whereby a second reaction mixture is produced;

treating said second reaction mixture with water, whereby a biphasic solution having an organic upper layer and an aqueous lower layer is produced; and wherein said organic upper layer comprises a solution of a 2,6-dicarbonylpyridine.

* * * * *